US 9,774,392 B2

United States Patent
Doucet et al.

(10) Patent No.: US 9,774,392 B2
(45) Date of Patent: Sep. 26, 2017

(54) SYSTEMS AND METHODS USING A POLARIMETER TO LOCALIZE STATE OF POLARIZATION TRANSIENTS ON OPTICAL FIBERS

(71) Applicant: Ciena Corporation, Hanover, MD (US)

(72) Inventors: David R. Doucet, Almonte (CA);
Douglas Charlton, Ottawa (CA);
David C. Bownass, Ottawa (CA);
Maurice S. O'Sullivan, Ottawa (CA);
Joanne Wakefield, Ottawa (CA)

(73) Assignee: Ciena Corporation, Hanover, MD (US)

( * ) Notice: Subject to any disclaimer, the term of this patent is extended or adjusted under 35 U.S.C. 154(b) by 6 days.

(21) Appl. No.: 14/865,802

(22) Filed: Sep. 25, 2015

(65) Prior Publication Data

US 2017/0019171 A1    Jan. 19, 2017

Related U.S. Application Data

(60) Provisional application No. 62/193,631, filed on Jul. 17, 2015.

(51) Int. Cl.
*H04B 10/08* (2006.01)
*H04B 10/00* (2013.01)
(Continued)

(52) U.S. Cl.
CPC ............ *H04B 10/0771* (2013.01); *G01J 4/00* (2013.01); *G01N 21/21* (2013.01); *G01N 21/23* (2013.01); *G02B 6/29311* (2013.01)

(58) Field of Classification Search
CPC .. H04B 10/0771; H04B 10/00; H04B 10/079; H04B 10/0705; H04B 10/25;
(Continued)

(56) References Cited

U.S. PATENT DOCUMENTS 7,106,979 B1 * 9/2006 Taylor ................ H04B 10/2569
398/209
7,139,476 B2 * 11/2006 Patel ...................... H04B 10/00
398/16

(Continued)

OTHER PUBLICATIONS

Qin et al., "New method for lightning location using optical ground wire," Chinese Optic Letters, vol. 4, No. 12, Dec. 10, 2006, pp. 712-714.

(Continued)

*Primary Examiner* — Ken N Vanderpuye
*Assistant Examiner* — Abbas H Alagheband
(74) *Attorney, Agent, or Firm* — Clements Bernard Walker PLLC; Christopher L. Bernard; Lawrence A. Baratta, Jr.

(57) ABSTRACT

Systems and methods using a polarimetric measurement device to localize a source of one or more State of Polarization (SOP) transients affecting one or more optical fibers are disclosed. The method includes transmitting a signal into a fiber in a first direction; receiving, at the polarimetric measurement device, the signal from one of the fiber and another fiber collocated in a bundle with the fiber in a second direction; and processing data from the polarimetric measurement device to determine a location of the one or more SOP transients. The processing can include detecting a presence of the one or more SOP transients based on a first signature and its echo seen in the data; and converting a time between the echoes into a distance.

20 Claims, 12 Drawing Sheets

(51) Int. Cl.
*H04B 10/06* (2006.01)
*G02F 1/035* (2006.01)
*G01N 21/00* (2006.01)
*G01J 4/00* (2006.01)
*H04B 10/077* (2013.01)
*G02B 6/293* (2006.01)
*G01N 21/23* (2006.01)
*G01N 21/21* (2006.01)

(58) Field of Classification Search
CPC ............ H04B 10/2572; H04B 10/2569; H04B 10/071; H04B 10/85; H04B 10/532; G01M 11/39; G01M 11/3181; G01M 11/336; G01M 11/3163; H04L 63/1416; G01D 5/35345; G01L 1/247; G01N 21/21; G01N 21/00; G06F 17/18; G02B 6/00; G02B 6/34; G02B 6/274; G02B 6/29319; G01J 3/28; G01J 4/00; A61B 5/1126; A61B 5/6892
USPC ...... 398/13, 65, 151, 184, 205, 209; 385/11; 356/73.1, 367
See application file for complete search history.

(56) References Cited

U.S. PATENT DOCUMENTS

| | | | |
|---|---|---|---|
| 7,155,128 B2 | 12/2006 | Roberts et al. | |
| 7,187,860 B2 * | 3/2007 | Bergano | H04B 10/2572 398/10 |
| 7,305,183 B2 | 12/2007 | Roberts et al. | |
| 7,693,357 B2 | 4/2010 | El Fellah et al. | |
| 7,693,359 B2 | 4/2010 | Murphy et al. | |
| 7,756,421 B2 | 7/2010 | Roberts et al. | |
| 7,903,977 B2 * | 3/2011 | MacDonald | H04B 10/85 398/152 |
| 8,233,755 B2 | 7/2012 | Murphy et al. | |
| 8,345,238 B2 | 1/2013 | Yao | |
| 8,364,036 B2 | 1/2013 | Boertjes et al. | |
| 8,594,499 B1 | 11/2013 | Roberts et al. | |
| 8,958,696 B2 | 2/2015 | Boertjes et al. | |
| 2002/0149823 A1 * | 10/2002 | Bergano | H04B 10/2572 398/20 |
| 2005/0276611 A1 * | 12/2005 | Patel | H04B 10/00 398/152 |
| 2006/0072922 A1 * | 4/2006 | MacDonald | H04B 10/85 398/152 |
| 2006/0153491 A1 * | 7/2006 | Murphy | H04B 10/071 385/13 |
| 2008/0044186 A1 * | 2/2008 | George | H04B 10/25754 398/115 |
| 2008/0062407 A1 * | 3/2008 | Boroditsky | H04B 10/85 356/73.1 |
| 2008/0144992 A1 * | 6/2008 | Thompson | A61B 5/1126 385/13 |
| 2010/0158433 A1 * | 6/2010 | Askins | G01M 11/088 385/13 |
| 2012/0281205 A1 * | 11/2012 | Askins | G01M 11/088 356/73.1 |
| 2013/0051809 A1 | 2/2013 | Mehrvar et al. | |
| 2014/0071436 A1 * | 3/2014 | Cyr | G01N 21/21 356/73.1 |
| 2014/0112660 A1 | 4/2014 | Al Sayeed et al. | |
| 2014/0328583 A1 | 11/2014 | Al Sayeed et al. | |
| 2015/0086195 A1 * | 3/2015 | Murphy | H04B 10/079 398/28 |
| 2016/0161397 A9 * | 6/2016 | Cyr | G01N 21/21 356/73.1 |

OTHER PUBLICATIONS

Kozlov et al., "Nonlinear repolarization dynamics in optical fibers: transient polarization attraction," HAL Archives-Ouvertes, Nov. 7, 2011, pp. 1-40.

Kramer et al., "Fiber Optic Sensor Network for Lightning Impact Localization and Classification in Wind Turbines," 2006 IEEE International Conference on Multisensor Fusion and Integration for Intelligent Systems, Sep. 3-6, 2006, pp. 1-6.

Reimer, "Simulation Methods for the Temporal and Frequency Dynamics of Optical Communication Systems," A thesis presented to the University of Waterloo in fulfilment of the thesis requirement for the degree of Doctor of Philosophy in Physics, 2012, pp. 1-199.

Guasoni et al., "Fast and Chaotic Fiber-Based Nonlinear Polarization Scrambler," pp. 1-11.

* cited by examiner

US 9,774,392 B2

SYSTEMS AND METHODS USING A POLARIMETER TO LOCALIZE STATE OF POLARIZATION TRANSIENTS ON OPTICAL FIBERS

CROSS-REFERENCE TO RELATED APPLICATION(S)

The present patent/patent application claims priority to U.S. Provisional Application No. 62/193,631, filed Jul. 17, 2015, and entitled "SYSTEMS AND METHODS USING A POLARIMETER TO LOCALIZE STATE OF POLARIZATION TRANSIENTS ON OPTICAL FIBERS," the contents of which are incorporated by reference.

FIELD OF THE DISCLOSURE

The present disclosure generally relates to fiber optic systems and methods. More particularly, the present disclosure relates to systems and methods using a polarimetric measurement device to localize State of Polarization (SOP) transients on optical fibers.

BACKGROUND OF THE DISCLOSURE

As bandwidth continues to grow, capacity is being stretched in fiber optic networks. Various advanced techniques are used to provide additional bandwidth including advanced coherent modulation techniques, polarization multiplexing, flexible grid spacing, and the like. With these advanced techniques, fiber optic systems suffer new degrees of susceptibility to transients on a time varying optical channel, including polarization transients, etc. As described herein, an SOP transient source causes an SOP transient which is anything that causes quick changes in the SOP of signals on an optical fiber. Coherent fiber optic systems are configured to track SOP changes as part of normal operation, but when quick SOP transients occur, these can be outside the tracking ability of fiber optic systems, leading to errors, loss of framing, etc. Example SOP transient sources can include, without limitation, external vibrations (e.g., bridges, roads, railroads, wind, etc.), bad splices on the optical fiber, weather (e.g., lighting, wind, etc.), or the like. Usually, SOP transient sources behave unpredictably and from unknown locations in the fiber. Further, SOP transient sources can be Time of Day specific, seasonal, etc. SOP transients can be particularly problematic with coherent transmission, and especially difficult to localize/isolate given their nature in general. That said, it would be advantageous to localize SOP transient sources so that proactive/preventative maintenance can occur.

Existing techniques to localize/isolate SOP transients can include a span-by-span determination based on faults or bit error rates in a coherent signal. However, these techniques only provide isolation to a specific span, which could be a few kilometers to over 100 km, and require actual faults or errors to identify. This is not enough resolution to perform preventative maintenance to root out the SOP transient source.

BRIEF SUMMARY OF THE DISCLOSURE

In an exemplary embodiment, a method using a polarimetric measurement device to localize a source of one or more State of Polarization (SOP) transients affecting one or more optical fibers includes, subsequent to transmitting a signal into a fiber, receiving, at the polarimetric measurement device, the signal from one of the fiber and a second fiber substantially collocated with the fiber; and processing data from the polarimetric measurement device to determine a location of the one or more SOP transients. The processing can include detecting a presence of the one or more SOP transients based on signatures and its echo seen in the data; and converting a time between the signatures and the echoe into a distance. The signal is looped back at a loop back point, and wherein the location is determined as a distance from the loop back point. The receiving can be from the fiber, and the signal is looped back with a circulator at a loop back point. The receiving can be from the second fiber, and the signal is looped back with a wavelength routing component at a loop back point. The signal can be received from the fiber at a loop back point, amplified at the loop back point, and transmitted back to the polarimetric measurement device. The polarimetric measurement device can operate in a trigger mode to enable identification for sequestration of polarimetric measurement device measurement records containing transients. The location can be determined with an accuracy directly related to a sample rate of the polarimetric measurement device. The method can further include intentionally causing an SOP transient to correlate fiber distance-based localization measurements to a physical position of the one or more optical fibers.

In another exemplary embodiment, a system to localize a source of one or more State of Polarization (SOP) transients affecting one or more optical fibers includes a polarimetric measurement device configured to receive light from one of the fiber and a second fiber substantially collocated with the fiber; and a processor configured to process data from the polarimetric measurement device to determine a location of the one or more SOP transients. The processor can be configured to detect a presence of the one or more SOP transients based on signatures and its echo seen in the data, and convert a time between the signatures and the echo into a distance. The light can be looped back at a loop back point, and wherein the location is determined as a distance from the loop back point. The polarimetric measurement device can receive the light from the fiber, and the light is looped back with a circulator at a loop back point. The polarimetric measurement device can receive the light from the second fiber, and the light is looped back with a wavelength routing component at a loop back point. The light can be received at a loop back point, amplified at the loop back point, and transmitted back to the polarimetric measurement device. The polarimetric measurement device can operate in a trigger mode to enable identification for sequestration of polarimeter measurement records containing transients. The location can be determined with an accuracy directly related to a sample rate of the polarimetric measurement device. An SOP transient can be intentionally caused to correlate fiber distance-based localization measurements to a physical position of the one or more optical fibers. The system can further include a source coupled to the fiber, wherein the source is configured to affect a rapid change of polarization of the light guided by the fiber.

In a further exemplary embodiment, a server configured to localize a source of one or more State of Polarization (SOP) transient affecting one or more optical fibers includes a processor; and memory storing instructions that, when executed, cause the processor to, subsequent to transmission of a signal in a first direction and reception of the signal in a second direction by a polarimetric measurement device, receive data from the polarimetric measurement device associated with the signal, process the data to detect the one or more SOP transients, and convert the data into a distance to localize the detected one or more SOP transients.

BRIEF DESCRIPTION OF THE DRAWINGS

The present disclosure is illustrated and described herein with reference to the various drawings in which like reference numbers are used to denote like system components/method steps, as appropriate, and in which.

DETAILED DESCRIPTION OF THE DISCLOSURE

Figure 1:
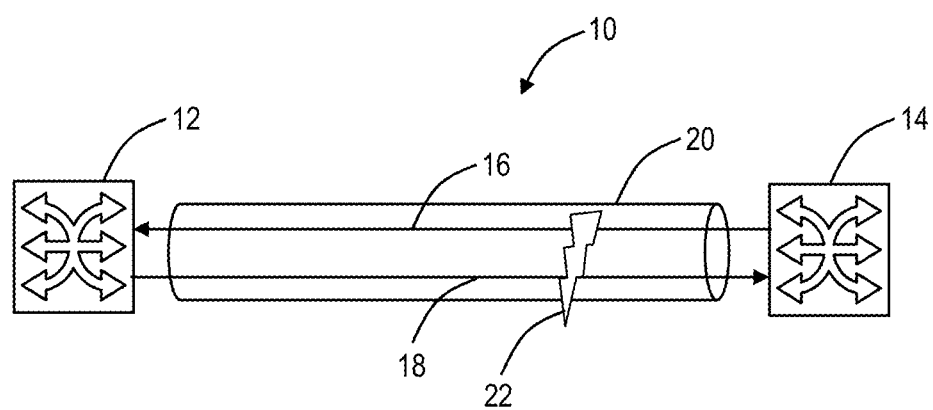
FIG. 1 is a network diagram of a network with two nodes interconnected by fibers each contained in a bundle.

In various exemplary embodiments, systems and methods are described using a polarimetric measurement device to localize State of Polarization (SOP) transients on optical fibers. The systems and methods utilize a device configured to perform polarimetric measurements to localize, to a high degree of accuracy, a point of a fiber disturbance that produces a transient (i.e., a large, fast change) in the state of polarization (SOP) of an optical signal. As described herein, such SOP transients can affect traffic in coherent detection systems, which must track SOP of the received signal in real time. The ability to track polarization depends on the specific implementation of a coherent receiver. The localization capability presented herein is thus important to troubleshooting an affected fiber network, to enable proactive and preventative maintenance on the fiber infrastructure.

In most, if not all, optical fiber deployments, a plurality of optical fibers are bundled together in a single fiber optic cable. This deployment characteristic is seen in all types of fiber optic deployments including long-haul, regional, metro, campus, submarine, etc. This is because a significant amount of cost associated with laying fiber optic cables is the physical costs, large fiber optical cable bundles are deployed with tens or hundreds of fiber optic cables in each bundle or conduit. Also, fiber optic systems are bidirectional—transmit and receive. In an exemplary aspect of the systems and methods, it has been observed that SOP transients affecting fiber optical cable bundles and associated fibers are observed from both transmission directions simultaneously or on different fibers simultaneously. The systems and methods leverage this fact with polarimeter measurements.

The systems and methods utilize a polarization state change, measured by the device configured to perform polarimetric measurements, as a form of signal for a time domain measurement. The time domain measurement determines how long it took before the polarization state change occurs, and enables transduction to distance since the propagation delay of light in the fiber optic cable can be mathematically determined. That is, the systems and methods use an "echo location" style of measurement—on one fiber (in both directions) or on two fibers in a same fiber optic cable bundle (in opposite directions) to localize SOP transients.

The measurement resolution of polarimeter technology can be from a few pec to sub-pec, giving localization resolution on the order of a few hundred meters to less than a meter. Of course, localization on the order of meters is a significant improvement over conventional techniques which can only isolate to a single span (several kilometers to over a hundred kilometers). With this resolution, preventative or proactive maintenance is possible. The nature of SOP measurement in the real fiber plant is such that correlation and often averaging techniques are required to discern a clear pattern for localization out of single transient measurements, which can be quite noisy.

Fiber Optic Network

Referring to FIG. 1, in an exemplary embodiment, a network diagram illustrates a network 10 with two nodes 12, 14 interconnected by fibers 16, 18 each contained in a bundle 20. Of course, those of ordinary skill in the art will recognize the network 10 can include additional node and bundles. The nodes 12, 14 can be any type of optical network element including, without limitation, Wavelength Division Multiplexing (WDM) terminals, Reconfigurable Optical Add/Drop Multiplexers (ROADMs), switches, routers, cross-connects, etc. In an exemplary embodiment, the nodes 12, 14 have optical transceivers or modems which connect to one another over the fibers 16, 18.

For example, each modem can be configured to use any of duobinary, quadrature amplitude modulation (QAM), differential phase shift keying (DPSK), differential quadrature phase shift keying (DQPSK), orthogonal frequency-division multiplexing (OFDM), polarization multiplexing with any of the foregoing, and any other type of coherent optical modulation and detection technique. For example, the modems can support various different baud through software programmability, e.g., the modems can support programmable modulation or constellations with both varying phase and/or amplitude. In an exemplary embodiment, a flexible optical modem can support multiple coherent modulation formats such as, for example, i) dual-channel, dual-polarization (DP) binary phase-shift keying (BPSK) for 100 G at submarine distances, ii) DP quadrature phase-shift keying (QPSK) for 100 G at ultra-long haul distances, iii) 16-quadrature amplitude modulation (QAM) for 200 G at metro to regional (600 km) distances), or iv) dual-channel 16-QAM for 400 G at metro to regional distances. Thus, in an exemplary embodiment, the same modem can support 100 G to 400 G. With associated digital signal processing (DSP) in the modem hardware, moving from one modulation format to another is completely software-programmable.

In another exemplary embodiment, the modem can support N-QAM modulation formats with and without dual-channel and dual-polarization where N can even be a real number and not necessarily an integer. Here, the modem can support non-standard speeds since N can be a real number as opposed to an integer, i.e. not just 100 G, 200 G, or 400 G, but variable speeds, such as 130 G, 270 G, 560 G, etc. These rates could be integer multiples of 50 Gb/s, 25 Gb/s, 10 Gb/s, or of 1 Gb/s. Furthermore, with the DSP and software programming, the capacity of the flexible optical modem can be adjusted upwards or downwards in a hitless manner so as to not affect the guaranteed rate. Additionally the modems can tune and arbitrarily select spectrum; thus no optical filters are required. Additionally, the modem can support various aspects of nonlinear effect mitigation and dispersion compensation (both for chromatic and polarization mode) in the electrical domain, thus eliminating external dispersion compensation devices, filters, etc. The modems can utilize Forward Error Correction (FEC) coding.

Thus, the nodes 12, 14 utilize coherent modulation/demodulation techniques and are thus susceptible to SOP transients. As described herein, conventional localization techniques only enable isolating a specific SOP transient to a single span, i.e., the bundle 20 between the nodes 12, 14. Unfortunately, this is on the order of kilometer resolution. It is not possible to troubleshoot an SOP transient with only kilometer resolution.

Note, the nodes 12, 14 communicate bidirectionally with one another, i.e., the node 12 transmits to the node 14 over the fiber 16 and the node 14 transmits to the node 12 over the fiber 18. Thus, an SOP transient source 22 acting on the bundle 20 will cause an SOP transient that is experienced on both the fibers 16, 18. Note, the SOP transient does not cause the same exact SOP changes on the different fibers 16, 18, but the overall form will be similar. Note, the fibers 16, 18 can be said to be substantially collocated with one another, i.e., located in the bundle 20 together, traveling along the same geographic route in a conduit, as overhead cable, etc. Of course, the fibers 16, 18 may have different paths inside a Central Office (CO) or the like, e.g., with different cabling from a Fiber Distribution Frame, etc. The substantially collocated means the fibers 16, 18, for the most part traverse a similar path between sites. Also, while the fibers 16, 18 are shown in a unidirectional transmission scheme, the systems and methods can also operate with bidirectional transmission on the same fiber.

Figure 2:
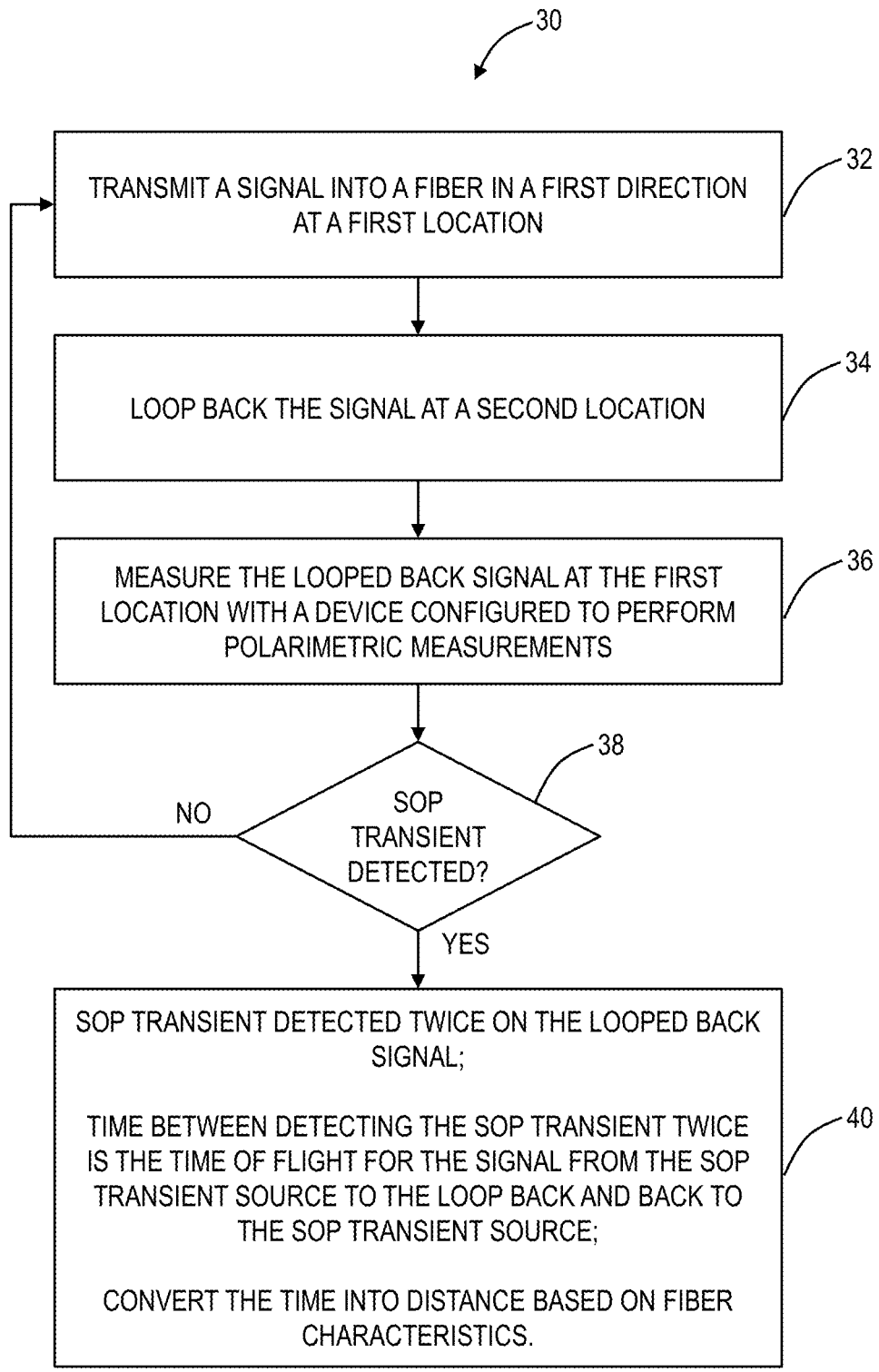
FIG. 2 is a flowchart of an SOP transient localization process utilizing a polarimetric measurement device to localize an SOP transient at a resolution of a few meters or less.

Localization Process with a Device Configured to Perform Polarimetric Measurements Referring to FIG. 2, in an exemplary embodiment, a flowchart illustrates an SOP transient localization process 30 utilizing a device configured to perform polarimetric measurements to localize an SOP transient at a resolution of a few meters or less. The SOP transient localization process 30 utilizes a polarimetric measurement device with a sampling interval on the order of a few is (e.g., 3 µs) or less and a polarized source providing a signal which is used to measure associated Stokes parameters to detect SOP changes. The signal does not carry information and can be referred to as a test tone, probe signal, etc. The polarimetric measurement device is configured to operate in a trigger mode with the polarized source to measure Stokes parameters; the trigger mode enables identification for sequestration of polarimeter measurement records containing transients.

Figure 3:
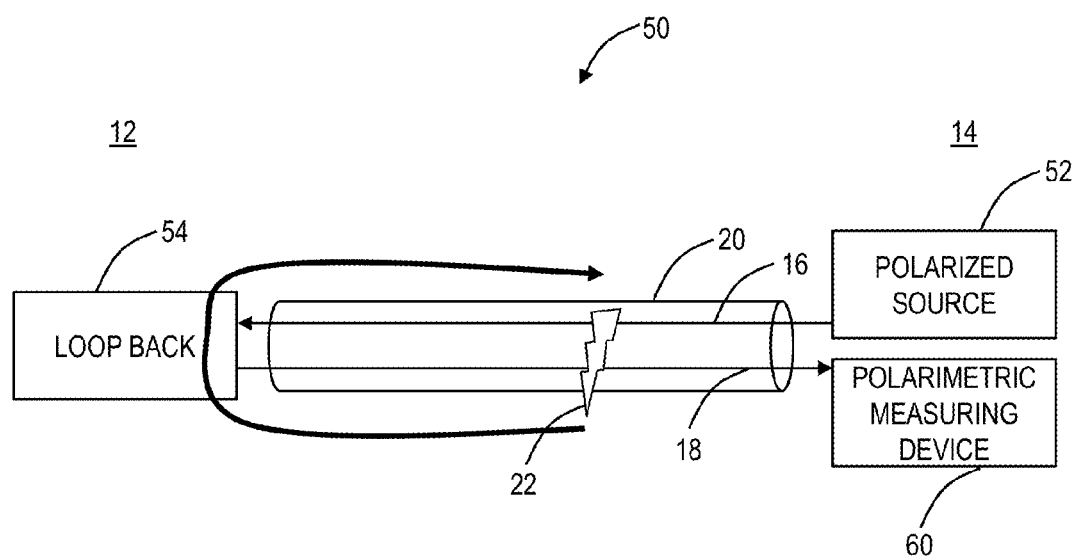
FIG. 3 is a network diagram of an exemplary setup for a two fiber mode.
Figure 4:
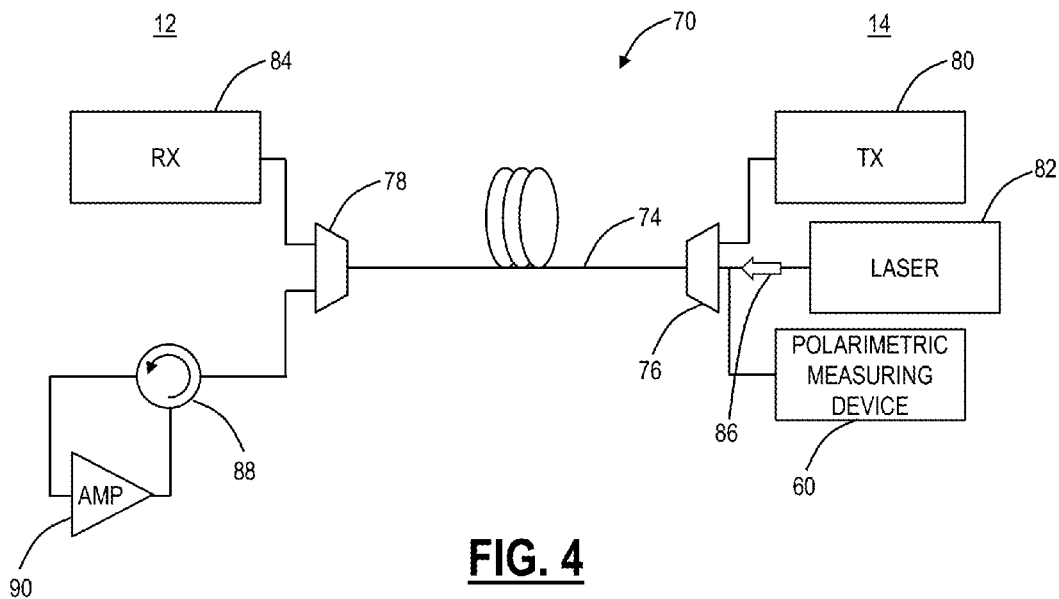
FIG. 4 is a network diagram of an exemplary setup for a one fiber mode.
Figure 5:
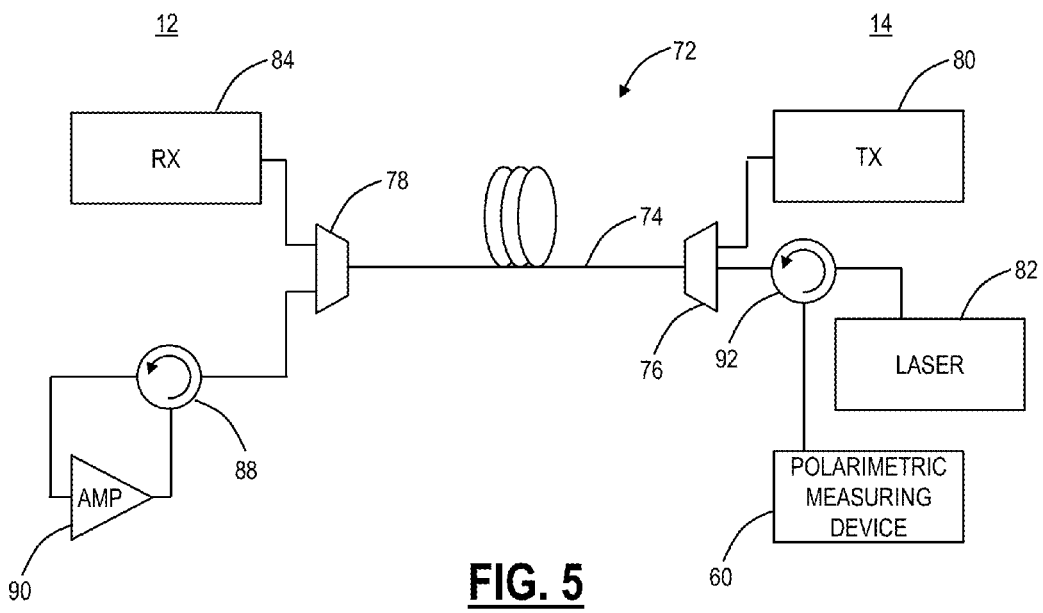
FIG. 5 is a network diagram of another exemplary setup for a one fiber mode.

The SOP transient localization process 30 includes transmitting a signal into a fiber in a first direction at a first location (step 32). At a second location (which is adjacent to the first location at the end of the fiber), the signal is looped backed to the first location (step 34). For example, the locations could be the nodes 12, 14. The SOP transient localization process 30 contemplates two different operating modes—a one fiber mode and a two fiber mode. An example of the two fiber mode is shown in FIG. 3 and two examples of the one fiber mode are shown in FIGS. 4-5. In either operating mode, the loop back functionality is configured to provide the signal back to the first location from the second location. Examples of the loop back functionality are described, for example, in FIGS. 3-5. The systems and methods contemplate any type of wavelength routing for the loop back functionality including circulators, Wavelength Selective Switches (WSSs), manual cabling to connect the ports, optical switches, and the like.

The loop back signal is measured at the first location with the polarimetric measurement device (step 36). The polarimetric measurement device can be a polarimeter configured to receive a polarized source or a coherent Digital Signal Processor (DSP) receiver performing polarimetric measurements from a coherent signal laser source. The SOP transient localization process 30 checks to detect an SOP transient (step 38). If there is an SOP transient detected, the SOP transient is detected twice in the looped back signal; time between detecting the SOP transient twice is the time of flight of the signal from the SOP transient source to the loop back and back to the SOP transient source; the SOP transient localization process 30 can include converting the time into distance based on fiber characteristics (step 40).

Again, any SOP transient will appear as two sequential polarization transients on a polarimeter capture—once from the signal and once from the looped back signal. The time between the polarization transients (these may not appear exactly the same, but multiple instances of transients can confirm a consistent time delta) is the time of flight of the optical signal from the SOP transient source to the loop back and back to the SOP transient source. This Round Trip Distance (RTD) is accurate to the sample rate of the polarimetric measurement device, which determines the accuracy of the RTD. Since the actual distance is ½ of RTD, the accuracy is also ½ of sample rate. This enables a specific determination of the expected accuracy, which in turn is useful once in the field to isolate the SOP transient source.

The conversion of time into the distance is also described in more detail herein. This conversion can be modified according to various conditions such as temperature, fiber type, wavelength, etc., but it is expected these variations should all lead to an error of less than 0.1% in the optical distance. Also, the calculated distance is provided as a fiber path distance from the loop back to the SOP transient source, and the actual geographic distance may vary, depending on installation details, such as fiber slack management policy.

In an exemplary embodiment, a method using a polarimetric measurement device to localize a source of one or more State of Polarization (SOP) transients affecting one or more optical fibers includes, subsequent to transmitting a signal into a fiber, receiving, at the polarimetric measurement device, the signal from one of the fiber and a second fiber substantially collocated with the fiber; and processing data from the polarimetric measurement device to determine a location of the one or more SOP transients. The processing can include detecting a presence of the one or more SOP transients based on signatures and its echo seen in the data in both a first direction and a second direction; and converting a time between the signatures and the echoes into a distance. The signal is looped back at a loop back point, and wherein the location is determined as a distance from the loop back point. The receiving can be from the fiber, and wherein the signal can be looped back with a circulator at a loop back point. The receiving can be from the second fiber, and wherein the signal can be looped back with a wavelength routing component at a loop back point. The signal can be received from fiber at a loop back point, amplified at the loop back point, and transmitted back to the polarimetric measurement device. The polarimetric measurement device can operate in a trigger mode to enable identification for sequestration of polarimetric measurement device measurement records containing transients. The location can be determined with an accuracy directly related to a sample rate of the polarimetric measurement device.

Two Fiber Mode Exemplary Setup

Referring to FIG. 3, in an exemplary embodiment, a network diagram illustrates an exemplary setup for a two fiber mode 50. FIG. 3 is similar to FIG. 1, with the bundle 20. The two fiber mode 50 includes a polarized source 52, at the node 14, coupled to the fiber 16; a loop back 54 at the node 12 configured to connect the fiber 16 to the fiber 18; and a polarimetric measurement device 60 at an end of the fiber 18. The loop back 54 can be anything which enables the fiber 16 to connect to the fiber 18, at the second location, i.e., a wavelength routing component. For example, the loop back 54 can be a fiber patchcord connecting the two fibers 16, 18, a ROADM port which automatically connects the two fibers 16, 18, a circulator, or the like. In some exemplary embodiments, the loop back 54 may include an amplifier if needed, to support the distance for the signal and the looped back signal over both the fibers 16, 18.

The polarized source 52 can be any wavelength, preferably a wavelength in the amplification band and is a single polarization laser source. By using a single polarization laser source connected to the transmit end of the fiber 16, with a loop back applied between the fibers 16, 18 at the loop back 54, the polarimetric measurement device 60 at the receive end of the fiber 18 can observe transients caused on both the fibers 16, 18. A transient occurring on or associated with the bundle 20 carrying both the fibers 16, 18 will thus be observed as two distinct transient excursions at the polarimetric measurement device 60. The first observation will propagate from the transient impact of the fiber 18. The transient impact of the fiber 16 will propagate to the loop back 54, and then along the full length of the fiber 18 to the polarimetric measurement device 60, appearing as a second transient on the polarimetric measurement device 60. The time difference between these two observed transients is the optical signal propagation time between the SOP transient source on the fiber 16 and the SOP transient source on the fiber 18. This fact allows a determination of the distance of the SOP transient source from the loop back 54, effectively localizing the SOP transient source.

In FIG. 3, for example, the configuration utilizes the polarized source 52 and the polarimetric measurement device 60 can be a polarimeter. In another exemplary embodiment, the same result can be achieved using a coherent signal laser source instead of the polarized source 52, with a coherent DSP receiver function performing polarimetric measurements, i.e., the polarimetric measurement device 60 is a coherent DSP receiver performing polarimetric measurements.

One Fiber Mode Exemplary Setups

Referring to FIGS. 4 and 5, in an exemplary embodiment, network diagrams illustrate exemplary setups for one fiber modes 70, 72. The two fiber modes 70, 72 include a single fiber 74, performing the same techniques as in FIGS. 2 and 3, through the use of optical circulator devices or the like at the source and loop back point. The exemplary setups of the one fiber modes 70, 72 include a multiplexer 76 at the node 14 and a demultiplexer 78 at the node 12, with the fiber 74 connected between the multiplexer 76 and the demultiplexer 78. The multiplexer 76 is configured to combine signals from various components for WDM transmission on the fiber 74, and the demultiplexer 78 is configured to split the signals from the fiber 74.

In these exemplary setups, the node 14 includes a transmitter (TX) 80, a laser 82, and the polarimetric measurement device 60, each communicatively coupled to the multiplexer 76. The node 16 includes a receiver (RX) 84 and a circulator 88, each communicatively coupled to the demultiplexer 78. The TX 80 is communicatively coupled to the RX 84, and can be a WDM data channel, such as at a wavelength on the ITU grid, a wavelength between about 1530 nm and 1565 nm, a flexible grid wavelength, or the like. Concurrently, with the channel formed by the TX 80 and the RX 84, the laser 82 can be used to provide a test signal over the fiber 74, for measurement by the polarimetric measurement device 60. The polarimetric measurement device 60 is communicatively coupled to the circulator 88 which is configured to loop back a signal, from the laser 82. The circulator 88 can optionally connect to an amplifier 90 if needed, to support the loop back. FIG. 4 has the laser 82 connected to the multiplexer 76 from the polarimetric measurement device 60, with an isolator 86 on the laser 82, while FIG. 5 has the laser 82 connected to the multiplexer 76 with the polarimetric measurement device 60 and through a circulator 92.

In this case, both directions of probe laser propagated on the same fiber 74. With the one fiber modes 70, 72, the SOP measurements can be quite noisy, so, statistical treatment of the test data is also required to arrive at an accurate measure of time/distance. This takes the form of autocorrelation of multiple transient measurements, which effectively averages out the noise from individual measurements when the Root Mean Square (RMS) average is performed on the set of autocorrelations from individual transients. Applying this mathematical treatment to the data brings out the portions of the response that are consistent across all transient measurements, and can show one or more sources for SOP transients, depending on the conditions of the fiber 74. Hence, multiple issues can be localized from a single set of measurements.

Again, in an exemplary embodiment, the laser 82 is a single polarization source and the polarimetric measurement device 60 is a polarimeter. In another exemplary embodiment, the laser 82 can be a coherent TX and the polarimetric measurement device 60 is a coherent RX function performing polarimetric measurements. In a further another exemplary embodiment, an Optical Service Channel (OSC) can be used as the single polarization probe, with the polarimetric measurement device 60 being a polarimeter. The OSC is configured to provide a service channel between locations in a fiber optic network. The OSC can operate at an OSC wavelength such as 1510 nm, 1625 nm, or the like. Note, using an OSC wavelength outside of the Erbium Doped Fiber Amplifier (EDFA) amplification range would dictate other amplifier technology such as Raman for the amplifier 90.

Localization System

In an exemplary embodiment, a system to localize a source of one or more State of Polarization (SOP) transients affecting one or more optical fibers includes a source coupled to a fiber, wherein the source is configured to affect a rapid change of polarization of light guided by the fiber; a polarimetric measurement device configured to receive the signal from one of the fiber and a second fiber substantially collocated with the fiber; and a processor configured to process data from the polarimetric measurement device to determine a location of the one or more SOP transients. The processor can be configured to detect a presence of the one or more SOP transients based on a first signature and its echo seen in the data in both a first direction and a second direction, and convert a time between the echoes into a distance. The signal can be looped back at a loop back point, and wherein the location is determined as a distance from the loop back point. The polarimetric measurement device can receive the signal from the fiber, and wherein the signal is looped back with a circulator at a loop back point. The polarimetric measurement device can receive the signal from the second fiber, and wherein the signal is looped back with a wavelength routing component at a loop back point. The signal can be received from the fiber at a loop back point, amplified at the loop back point, and transmitted back to the polarimetric measurement device. The polarimetric measurement device can operate in a trigger mode to enable identification for sequestration of polarimetric measurement device measurement records containing transients. The location can be determined with an accuracy directly related to a sample rate of the polarimetric measurement device.

In-Service and Out-of-Service Measurements

The SOP transient localization process 30 can be implemented both on an out-of-service network 10 or an in-service network 10. Further, the configurations of FIGS. 3, 4, and 5 support operation in-service or out-of-service. In the out-of-service case, the SOP transient localization process 30 can be performed for fiber characterization, while in-service, the SOP transient localization process 30 can be performed for maintenance. Of course, other embodiments are contemplated. When implemented out-of-service, the probe source 52 or the like can use any wavelength, while when implemented in-service, the probe source 52 or the laser 82 can be a wavelength that does not interfere with any existing channels.

Time to Distance Calculations

Again, the output of the polarimetric measurement device 60 is a time difference between the SOP transient source first encountered on a first trip and the SOP transient source encountered on the return trip. First, the speed of the optical signal needs to be determined over the fibers 16, 18, 74. The index of refraction (or refractive index) is a way of measuring the speed of light in a material. Light travels fastest in a vacuum, such as in outer space. The speed of light in a vacuum is about 300,000 kilometers per second (or more precisely 299,792,458 m/s). The refractive index of a medium is calculated by dividing the speed of light in a vacuum by the speed of light in that medium. The refractive index of a vacuum is therefore 1, by definition. A typical single-mode fiber used for telecommunications has a cladding made of pure silica, with an index of 1.444 at 1500 nm, and a core of doped silica with an index around 1.4475. The larger the index of refraction, the slower light travels in that medium. From this information, a simple rule of thumb is that a signal using optical fiber for communication will travel at around 200,000 kilometers per second (or more precisely 207,110,506 m/s which is 299,792,458 m/s divided by 1.4475). For purposes of a time to distance calculation, the 200,000 km/s can be changed to 5 µs/km (for the foregoing descriptions, the actual value used is 4.9 µs/km which is a bit more accurate). This 4.9 µs/km can be referred to as a time-to-distance conversion factor. Those of ordinary skill in the art will recognize it is possible to calculate the time-to-distance conversion factor for different types of fiber, as described herein.

Assume, for an example, the time difference is 200 µs apart—this represents the round trip time of flight between the SOP transient source, the loop back point, and the SOP transient source again. The fiber distance from the loop back 54 to the SOP transient source is:

$$\text{Distance} = \frac{\frac{200 \text{ µs}}{4.9 \text{ µs}}}{2} \text{km} = \sim 20.4 \text{ km}$$

With a sample rate of 3 µs on the polarimeter 60, the above value of 20.4 km is accurate to:

$$\text{Distance Accuracy} = \frac{\frac{3 \text{ µs}}{4.9 \text{ µs}}}{2} \text{km} = \sim 300 \text{ m}$$

This accuracy is orders of magnitude better than conventional span-by-span isolation techniques. Thus, the SOP transient source in the above example is located somewhere between ~20.15 km and 20.5 5km from the loop back 54.

A generalized formula to determine the distance of the SOP transient source to the loop back 54, given the time from the polarimetric measurement device 60 is as follows:

$$\text{Distance} = \frac{\frac{\text{time in µs}}{\text{TD conversion}}}{2} \text{km}$$

where TD conversion is the time-to-distance conversion factor, i.e., 4.9 µs.

Thus, the systems and methods essentially involves observation of an SOP transient event in a single fiber link that is looped back, such that an 'echo' of the event can be seen, hence location can be determined in fiber distance, by measuring the time of flight difference between the original and 'echo' transient using a polarimetric measurement device with sufficient time resolution.

Fiber Distance vs. Geographical Distance

It is important to note that this distance is fiber distance, and would include any slack fiber, dispersion compensating fiber, changes in elevation, etc. and may not match geographical distance. However, this can be overcome as described herein, by matching fiber distance to the geographical distance through calibration. Thus, while knowing the fiber distance would seem to be all that is necessary to localize the SOP transient source, there is still the issue of relating the fiber distance to actual physical location on the fiber link. Specifically, fiber distance and geographic distance will not be equal due to, for example, fiber slack storage, altitude changes, cable spiral, and the like. That is, the aforementioned items can contribute to modifying the relationship to geographic distance.

This leads to a problem statement—how to relate fiber distance-based localization measurements to a physical position in an actual network? With the SOP transient localization process 30, there is a technique to localize transients. It can be observed that one could force generation of an SOP transient in the field, at a known location, to determine fiber distance for that point. Thus, the systems and methods can include a so-called SOP transient generation tool to act as a known SOP transient source, at a known physical location. With the known SOP transient source, the SOP transient localization process 30 can be performed to provide actual fiber distance to a known physical location—this in turn can be used to correlate fiber distance to geographical distance. For example, as part of the SOP transient localization process 30, an SOP transient can be intentionally caused to correlate fiber distance-based localization measurements to a physical position of the one or more optical fibers.

In an exemplary embodiment, the SOP transient generation tool can be an impact tool or an apparatus to deliver a controlled impact/magnetic field. The SOP transient generation tool is configured to act on the bundle 20 and/or the fibers 16, 18, 74, at corresponding breakout points where access to the fibers 16, 18, 74 is available. The impact tool can be a manual, physical device, such as a hammer or mallet. Of course, a manual, physical device is not well controlled, leading to a risk of impacts to traffic if the SOP transient is too fast/large. That is, the SOP transient generation tool must not cause SOP tracking concerns for in-service modems. Note, different bundles 20 or fibers 16, 18, 74 may have different sensitivity to impact. In an exemplary embodiment, the impact tool can have some form of firm attachment to the bundle 20 or fibers 16, 18, 74 to deliver a controlled force. The impact tool must be able to deliver multiple impacts with consistent force, portability is preferred, the impact tool cannot damage the bundle 20 or fibers 16, 18, 74.

The apparatus to deliver a controlled impact/magnetic field can use a coil around the bundle 20 or fibers 16, 18, 74 to generate a magnetic field impulse, using Faraday effect to cause SOP transient on fibers 16, 18, 74. In an exemplary embodiment, the apparatus can be realized via a manually wrapped coil with a few loops due to the challenge of keeping the fiber 16, 18, 74 intact (no traffic disruption). In another exemplary embodiment, the apparatus can be a clamp-on coil. The apparatus, unlike the impact tool, does need electrical power and some kind of control unit to apply impulses. However, the apparatus has significantly less risk of damage to the fiber 16, 18, 74 relative to the impact tool.

Exemplary Operation—Two-Fiber Setup

Referring to FIGS. 6-15, in various exemplary embodiments, graphs illustrate polarimeter readings from an exemplary operation using the two-fiber setup of FIG. 3.

Figure 6:
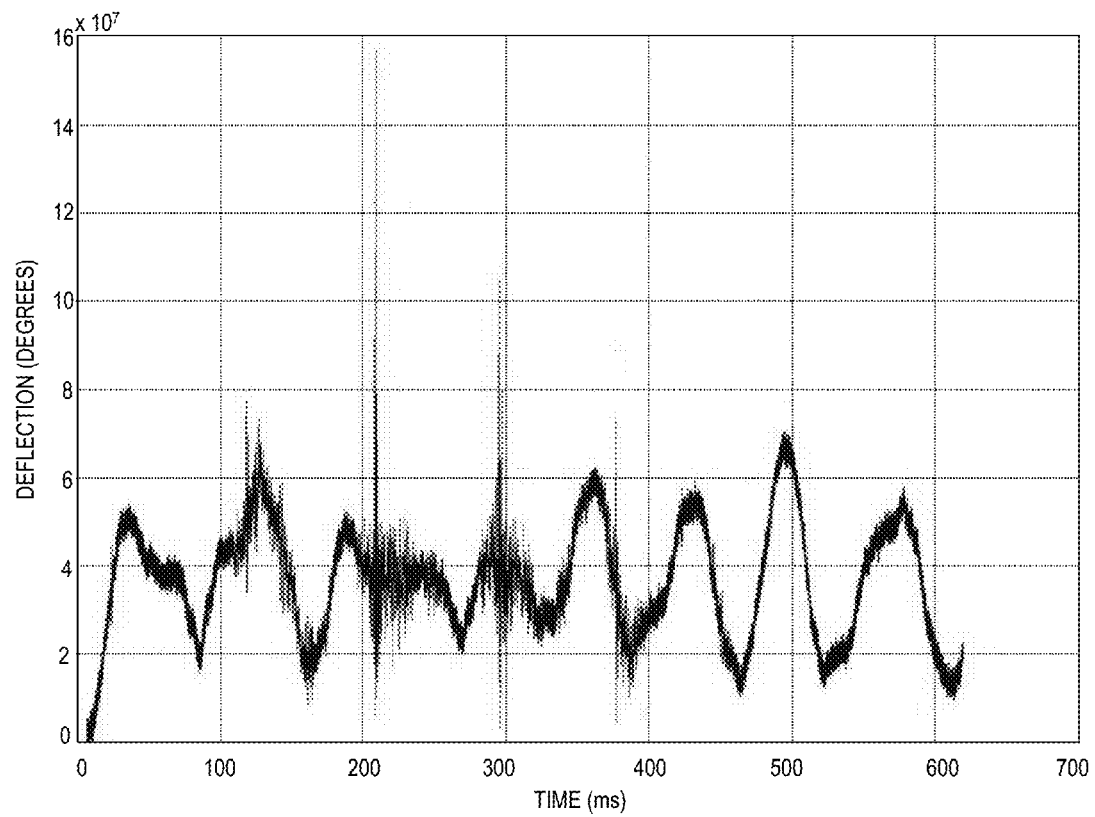
FIG. 6 is a polarimetric measurement device trace, triggered at 5° and 0.6 s records.

FIG. 6 is a polarimetric measurement device trace, triggered at 5° and 0.6 s records. This example shows 400+ records. The transients are harvested (+/−1 ms) and an autocorrelation is performed along with the sum of the squares of the autocorrelations to look for/locate any surviving echo.

Figure 7:
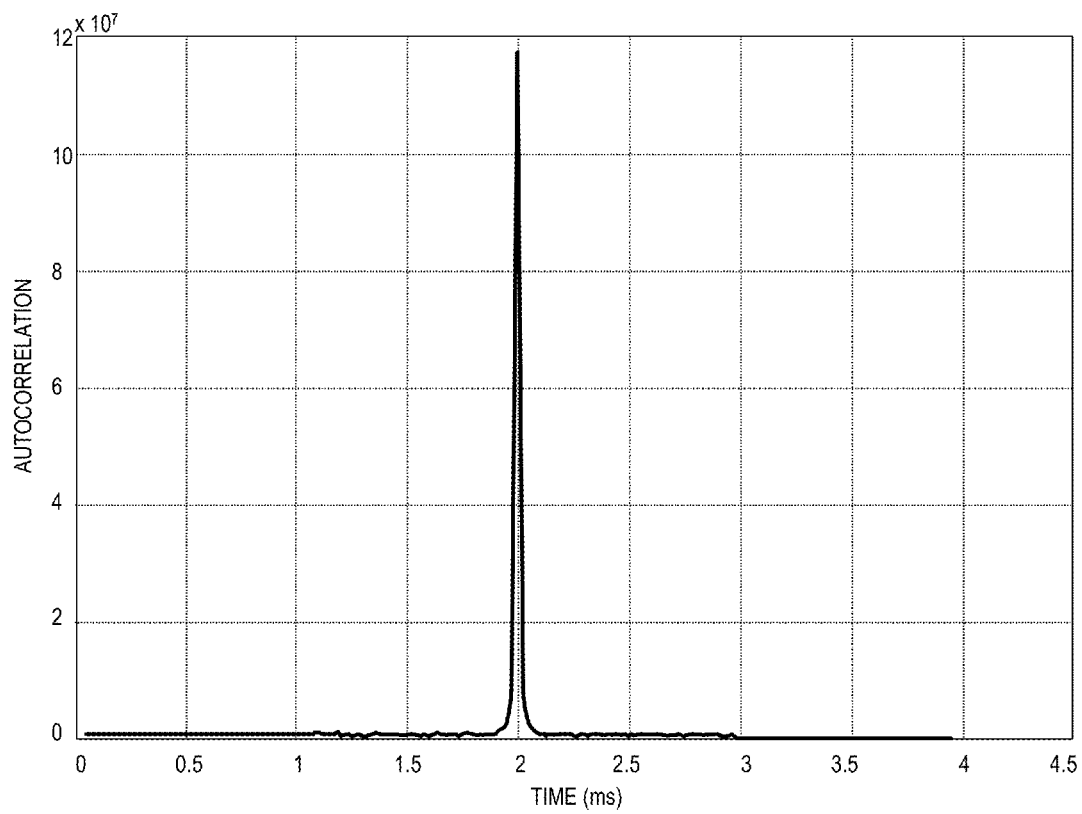
FIG. 7 is a graph of autocorrelations of records for a non-looped back configuration.

FIG. 7 is a graph of autocorrelations of records for a non-looped back configuration. Note, FIG. 7 illustrates no evidence of echo, from the autocorrelations of about 400 records. FIG. 7 further illustrates the loop back configuration is required to detect echoes.

Figure 8:
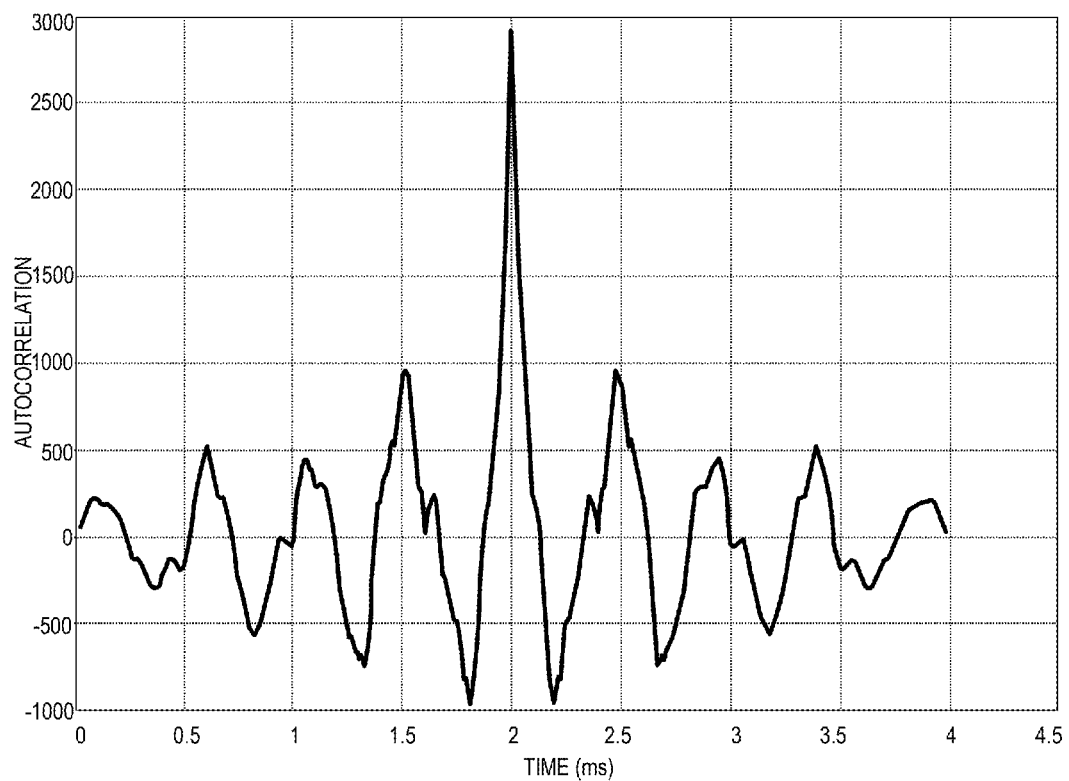
FIG. 8 is a polarimetric measurement device trace, on a looped back configuration.

FIG. 8 is a polarimetric measurement device trace, on a looped back configuration, compared to FIG. 7. Note, there is lots of structure in the wings, most of which is unrelated to an echo signature.

Figure 9:
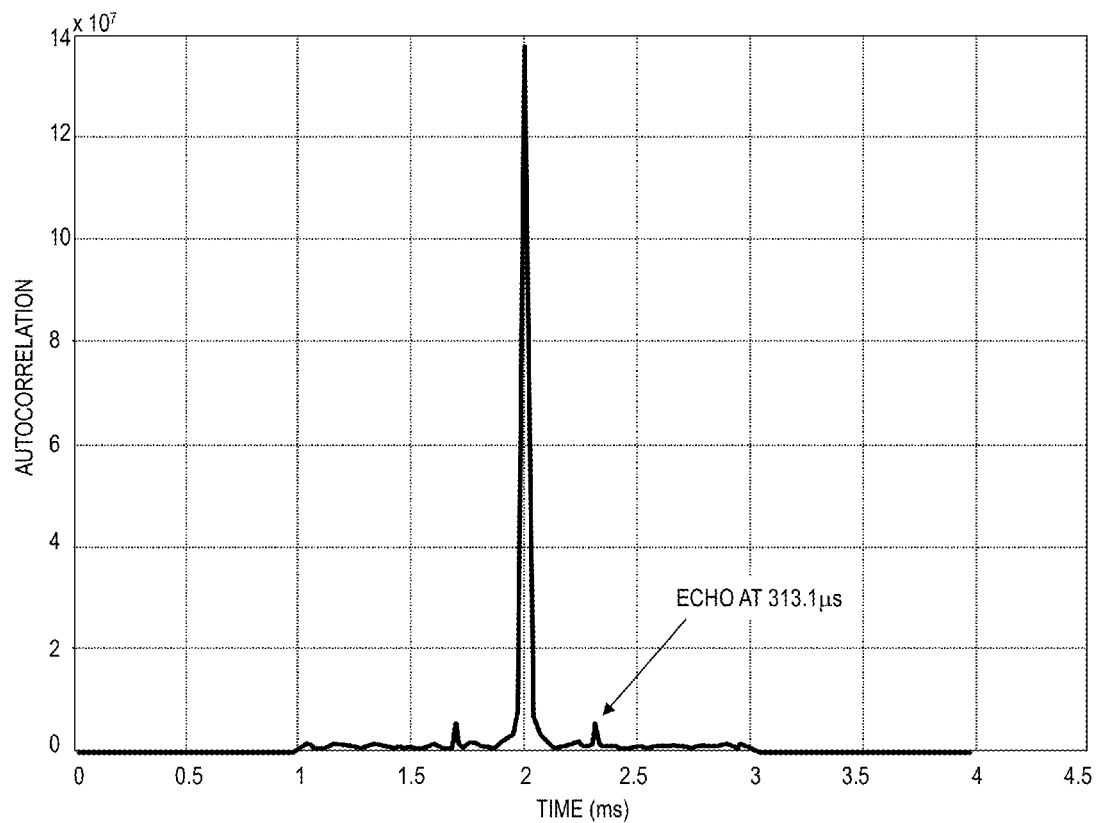
FIG. 9 is a graph of processed loop back autocorrelations for the first 100 records, showing echo from the polarimetric measurement device trace of FIG. 8.

FIG. 9 is a graph of processed loop back autocorrelations for the first 100 records, showing echo. Note, an echo is detected at 313.1 μs.

Figure 10:
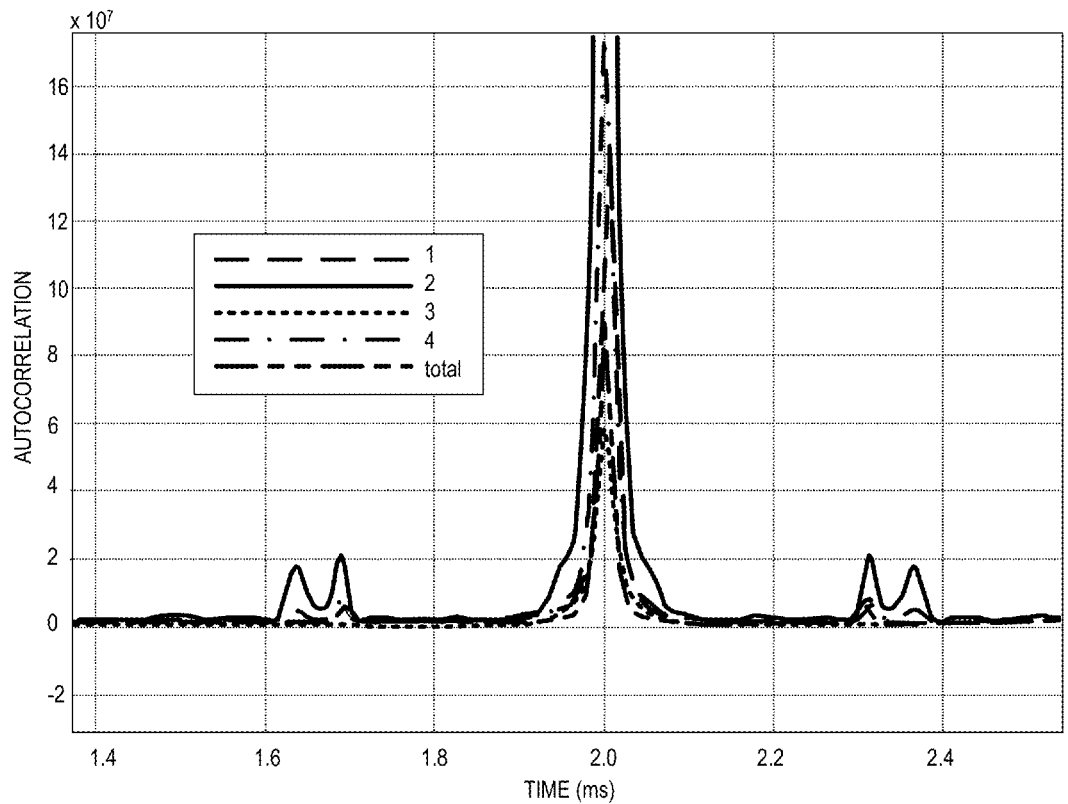
FIG. 10 is a graph of the average of the sum of autocorrelations squared over a sequential group of records.

FIG. 10 is a graph of the average of the sum of autocorrelations squared over a sequential group of records. First, the different groups 1-4 were done at different times as follows:

| Group | Start Time | End Time |
|---|---|---|
| 1 | 5/9/2014 9:55:00 AM | 5/10/2014 7:49:00 AM |
| 2 | 5/10/2014 7:51:00 AM | 5/10/2014 10:26:00 AM |
| 3 | 5/10/2014 10:27:00 AM | 5/11/2014 3:55:00 PM |
| 4 | 5/11/2014 3:58:00 PM | 5/12/2014 8:24:00 AM |

All experiments show echo at 313.1 μs with additional echo at 367.6 μs appearing in the second of the sequence. Also, there is some evidence of a third (small) peak at 341.4 μs.

Figure 11:
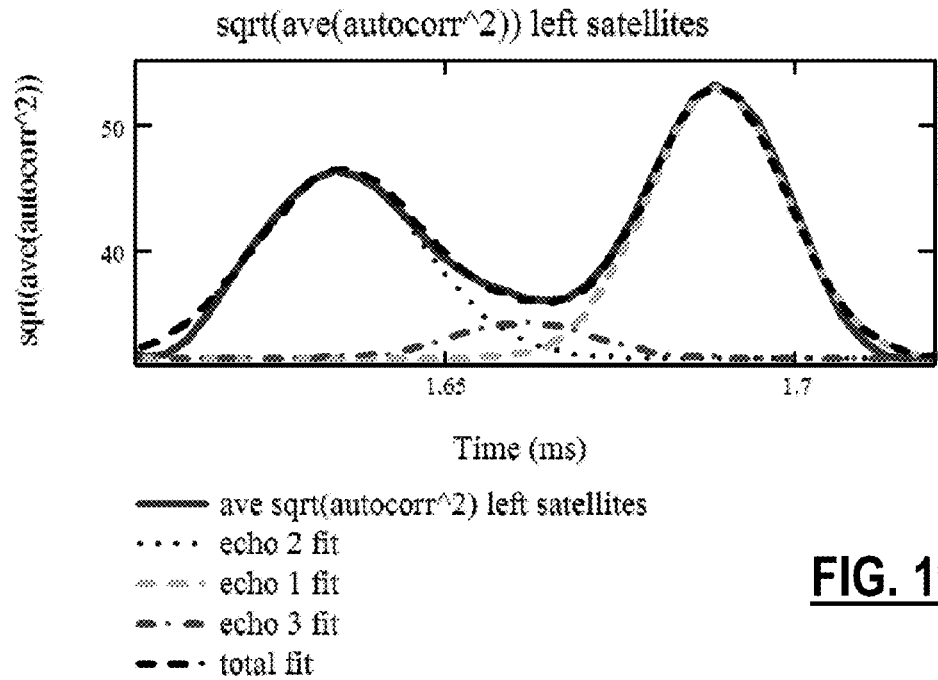
FIGS. 11 and 12 are graphs fitting to satellites of the total data set.
Figure 12:
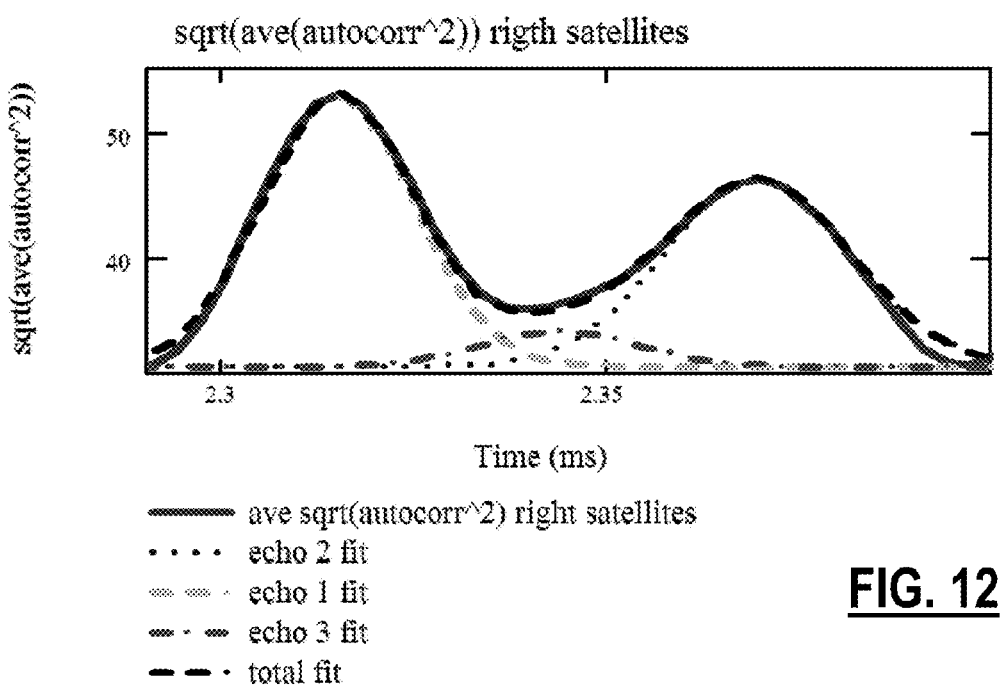

FIGS. 11 and 12 are graphs fitting to satellites of the total data set. This data has the following echoes:

Echo 1 (left-right)=626.2 μs
Echo 2 (left-right)=735.2 μs
Echo 3 (left-right)=682.8 μs In this example, the round trip distance is 92.75 km and using the formula:

$$Distance = \frac{\frac{time\ in\ \mu s}{4.9\ \mu s}}{2} km,$$

The distances are:
Round trip echo 1 distance=63.9 km
Round trip echo 2 distance=75.1 km
Round trip echo 3 distance=69.7 km Note, since each of the above distances is "round trip," these need to be divided by 2 again. Since the overall round trip distance (92.75 km) and the roundtrip echo distances are known, it is possible to determine the echo distance from the loop back as follows:

Echo 1=14.4 km (all groups largest peak)
Echo 2=8.9 km (group 2 only second largest peak)
Echo 3=11.5 km (group 2 only smallest peak)

Here, Echo 1=(97.75 km−63.9 km)/2=14.4 km, Echo 2=(97.75 km−75.1 km)/2=8.9 km, and Echo 3 (97.75 km−69.7 km)/2=11.5 km.

Figure 13:
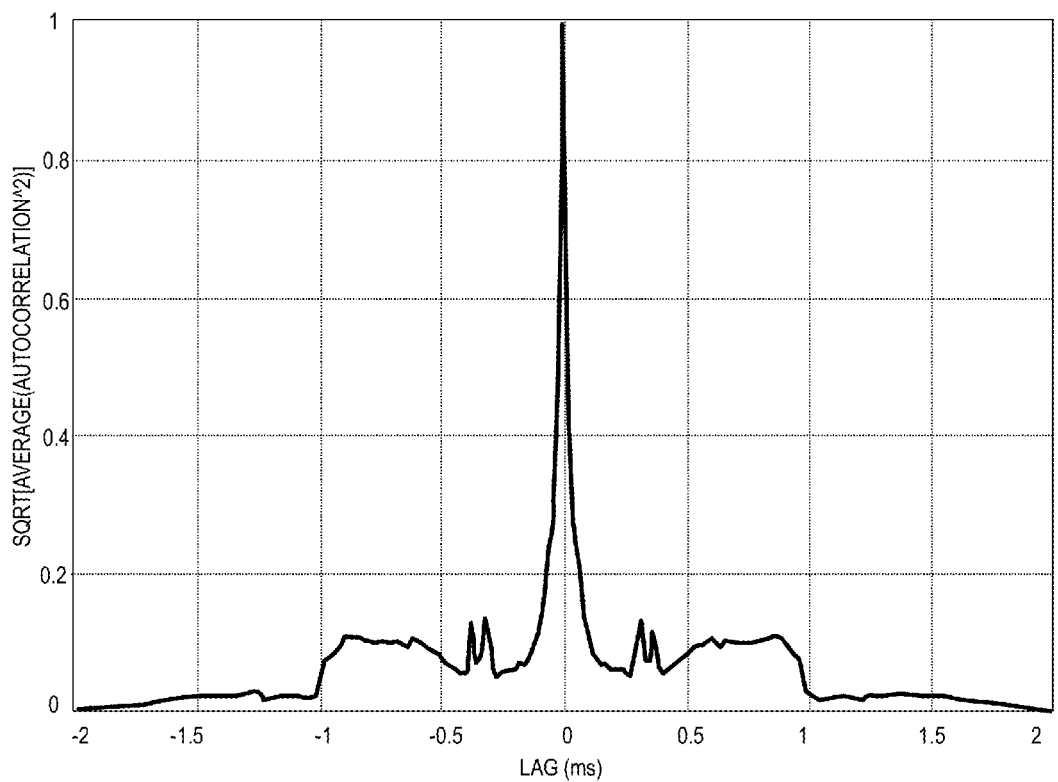
FIG. 13 is a graph of the average of the sum of autocorrelations squared over time.

FIG. 13 is a graph of the average of the sum of autocorrelations squared over time. Note, there are multiple echo peaks, and extra peaks only present in a single interval as in the first loop back.

Round trip distance=92.75 km
Round trip echo 1 distance=64.6 km
Round trip echo 2 distance=76.8 km
Round trip echo 3 distance=70.7 km
Round trip echo 4 distance=60.6 km From these values, the distance from the loop back is:
Echo 1=14.1 km (all groups largest peak)
Echo 2=8.0 km (isolated occurrence second largest peak)
Echo 3=11.0 km (isolated occurrence third largest peak)
Echo 4=16.1 km (isolated occurrence smallest peak)

Figure 14:
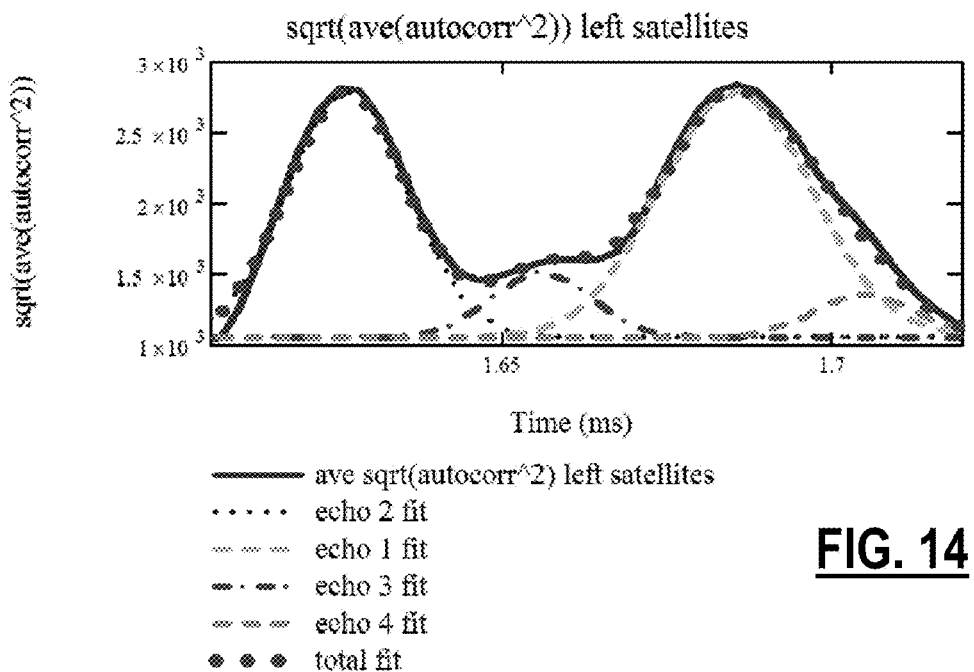
FIGS. 14 and 15 are graphs fitting to satellites of the total data, for the exemplary operation in FIG. 13.
Figure 15:
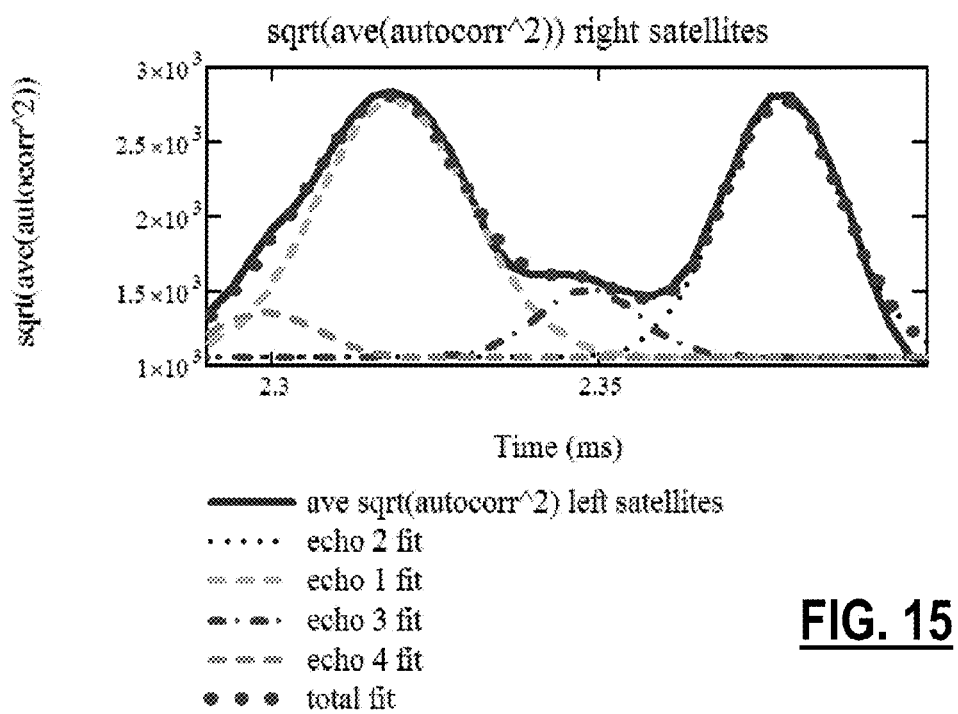

FIGS. 14-15 are graphs fitting to satellites of the total data set, for the Echoes 1-4 above. This data has the following echoes:

Echo 1 (left-right)=633.2 μs
Echo 2 (left-right)=752.2 μs
Echo 3 (left-right)=692.8 μs
Echo 4 (left-right)=594 μs Server In an exemplary embodiment, a server configured to localize a source of one or more State of Polarization (SOP) transient affecting one or more optical fibers includes a processor; and memory storing instructions that, when executed, cause the processor to, subsequent to transmission of a signal in a first direction and reception of the signal in a second direction by a polarimetric measurement device, receive data from a polarimetric measurement device associated with the signal, process the data to detect the one or more SOP transients, and convert the data into distance to localize the detected one or more SOP transients. The processor can be configured to detect a presence of the one or more SOP transients based on a first signature and its echo seen in the data in both the first direction and the second direction, and convert a time between the echoes into a distance. The signal can be looped back at a loop back point, and wherein the distance is determined from the loop back point. The polarimetric measurement device can receive the signal from a same fiber as the transmission, and wherein the signal is looped back with a circulator at a loop back point. The polarimetric measurement device can receive the signal from a different fiber from the transmission, and wherein the signal is looped back with a wavelength routing component at a loop back point. The polarimetric measurement device can operate in a trigger mode to enable identification for sequestration of polarimetric measurement device measurement records containing transients. The distance can be determined with an accuracy directly related to a sample rate of the polarimetric measurement device.

In performing the SOP transient localization process 30, it will be appreciated that some exemplary embodiments described herein may include one or more generic or specialized processors ("one or more processors") such as microprocessors, digital signal processors, customized processors, and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the aforementioned approaches may be used. Moreover, some exemplary embodiments may be implemented as a non-transitory computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer readable medium, software can include instructions executable by a processor that, in response to such execution, cause a processor or any other circuitry to perform a set of operations, steps, methods, processes, algorithms, etc.

Although the present disclosure has been illustrated and described herein with reference to preferred embodiments and specific examples thereof, it will be readily apparent to those of ordinary skill in the art that other embodiments and examples may perform similar functions and/or achieve like results. For example, rather than a single polarization laser source and polarimeter based on optical power measurements, another embodiment can achieve the same result through use of a coherent signal laser source, with a coherent DSP receiver function performing polarimetric measurements. All such equivalent embodiments and examples are within the spirit and scope of the present disclosure, are contemplated thereby, and are intended to be covered by the following claims.

What is claimed is:

1. A method using a polarimetric measurement device to localize a source of one or more State of Polarization (SOP) transients affecting one or more optical fibers, the method comprising:
   subsequent to transmitting a signal into a first fiber, receiving, at the polarimetric measurement device, the signal from one of the first fiber and a second fiber, wherein, when the signal is received from the second fiber, the second fiber is substantially collocated with the first fiber, and wherein the signal is looped back at a loop back point into the one of the first fiber and the second fiber; and
   processing data from the polarimetric measurement device to determine a location of the one or more SOP transients based on the signal experiencing the one or more SOP transients twice due to the loop back.

2. The method of claim 1, wherein the processing comprises:
   detecting a presence of the one or more SOP transients based on signatures and its echo seen in the data; and
   converting a time between the signatures and the echos into a distance.

3. The method of claim 1, wherein the location is determined as a distance from the loop back point.

4. The method of claim 1, wherein the receiving is from the first fiber, and wherein the signal is looped back with a circulator at a loop back point.

5. The method of claim 1, wherein the receiving is from the second fiber, and wherein the signal is looped back with a wavelength routing component at a loop back point.

6. The method of claim 1, wherein the signal is received from the first fiber at the loop back point, amplified at the loop back point, and transmitted back to the polarimetric measurement device.

7. The method of claim 1, wherein the polarimetric measurement device operates in a trigger mode to enable identification for sequestration of polarimetric measurement device measurement records containing transients.

8. The method of claim 1, wherein the location is determined with an accuracy directly related to a sample rate of the polarimetric measurement device.

9. The method of claim 1, further comprising:
   intentionally causing an SOP transient to correlate fiber distance-based localization measurements to a physical position of the one or more optical fibers.

10. A system to localize a source of one or more State of Polarization (SOP) transients affecting one or more optical fibers, the system comprising:
    a polarimetric measurement device configured to receive light from one of a first fiber and a second fiber, wherein, when the light is received from the second fiber, the second fiber is substantially collocated with the first fiber, and wherein the light is looped back at a loop back point into the one of the first fiber and the second fiber; and
    a processor configured to process data from the polarimetric measurement device to determine a location of the one or more SOP transients based on the light experiencing the one or more SOP transients twice due to the loop back.

11. The system of claim 10, wherein the processor is configured to detect a presence of the one or more SOP transients based on signatures and its echo seen in the data, and convert a time between the signatures and the echo into a distance.

12. The system of claim 10, wherein the location is determined as a distance from the loop back point.

13. The system of claim 10, wherein the polarimetric measurement device receives the light from the first fiber, and wherein the light is looped back with a circulator at a loop back point.

14. The system of claim 10, wherein the polarimetric measurement device receives the light from the second fiber, and wherein the light is looped back with a wavelength routing component at a loop back point.

15. The system of claim 10, wherein the light is received at a loop back point, amplified at the loop back point, and transmitted back to the polarimetric measurement device.

16. The system of claim 10, wherein the polarimetric measurement device operates in a trigger mode to enable identification for sequestration of polarimetric measurement device measurement records containing transients.

17. The system of claim 10, wherein the location is determined with an accuracy directly related to a sample rate of the polarimetric measurement device.

18. The system of claim 10, wherein an SOP transient is intentionally caused to correlate fiber distance-based localization measurements to a physical position of the one or more optical fibers.

19. The system of claim 10, further comprising:

a source coupled to the fiber, wherein the source is configured to affect a rapid change of polarization of the light guided by the fiber.

20. A server configured to localize a source of one or more State of Polarization (SOP) transient affecting one or more optical fibers, the server comprising:

a processor; and memory storing instructions that, when executed, cause the processor to subsequent to transmission of a signal in a first direction and reception of the signal in a second direction by a polarimetric measurement device, receive data from the polarimetric measurement device associated with the signal, wherein the signal is looped back at a loop back point into the one or more optical fibers, process the data to detect the one or more SOP transients, and convert the data into a distance to localize the detected one or more SOP transients based on the signal experiencing the one or more SOP transients twice due to the loop back.

* * * * *